(12) United States Patent
Chen

(10) Patent No.: US 11,471,909 B2
(45) Date of Patent: Oct. 18, 2022

(54) AROMATHERAPY DIFFUSER

(71) Applicant: ETEKCITY CORPORATION, Anaheim, CA (US)

(72) Inventor: Jiao Chen, Shenzhen (CN)

( * ) Notice: Subject to any disclaimer, the term of this patent is extended or adjusted under 35 U.S.C. 154(b) by 796 days.

(21) Appl. No.: 16/442,293

(22) Filed: Jun. 14, 2019

(65) Prior Publication Data

US 2020/0390996 A1   Dec. 17, 2020

(51) Int. Cl.
 *A61L 9/12*   (2006.01)
 *B05B 17/06*  (2006.01)
 *A61M 21/00*  (2006.01)
 *A61M 11/00*  (2006.01)
 *A61L 9/22*   (2006.01)

(52) U.S. Cl.
 CPC ............ *B05B 17/06* (2013.01); *A61L 9/12* (2013.01); *A61L 9/22* (2013.01); *A61M 11/005* (2013.01); *A61M 21/00* (2013.01); *A61L 2209/111* (2013.01); *A61L 2209/132* (2013.01); *A61M 2021/0016* (2013.01); *Y10S 261/48* (2013.01); *Y10S 261/88* (2013.01)

(58) Field of Classification Search
 CPC ..... A61L 9/12; A61L 9/14; A61L 9/16; A61L 9/22; A61L 2209/111; A61L 2209/132; Y10S 261/48; Y10S 261/88
 See application file for complete search history.

(56) References Cited

U.S. PATENT DOCUMENTS

2005/0169812 A1* 8/2005 Helf ................. G02B 6/0068
                                                422/123
2021/0052763 A1* 2/2021 Guo ................... A61L 9/127

* cited by examiner

*Primary Examiner* — Timothy C Cleveland
(74) *Attorney, Agent, or Firm* — Tsz Lung Yeung

(57) ABSTRACT

An aromatherapy diffuser includes a diffuser body and a diffusion device. The diffuser body has an oil storage cavity for storing a predetermined amount of essential oil. The diffusion device is supported in the diffuser body, and includes an ultrasonic vibrator arranged to generate ultrasonic vibrations, in such a manner that when the diffusion body is partially immersed in the water stored in the container, the essential oil is released to the water from the oil storage cavity while the ultrasonic vibrator is arranged to cause ultrasonic vibrations in the water so as to agitate the water molecules for releasing negatively charged mist and essential oil into ambient air.

12 Claims, 5 Drawing Sheets

AROMATHERAPY DIFFUSER

BACKGROUND OF THE PRESENT INVENTION

Field of Invention

The present invention relates to a diffuser, and more particularly to an aromatherapy diffuser which does not have a built-in water tank. Rather, the aromatherapy diffuser is capable of agitating water which is stored in a separately provided container for allowing a user to diffuse water and essential oil whenever necessary.

Description of Related Arts

A conventional aromatherapy diffuser usually comprises a main body, a water tank for storing a predetermined amount of water and essential oil, and an ultrasonic diffuser supported in the main body. The ultrasonic diffuser may break down the water and essential oil particles to form negatively charged ions and mists. The mists are then discharged out of the main body and released into ambient air.

There are several disadvantages in association with the above-mentioned conventional aromatherapy diffuser. First, an aromatherapy diffuser having a built-in water tank will usually have a relatively larger size. This is because the size of the water tank cannot be too small. Otherwise, frequent re-filling of water will be required. When the size of the water tank cannot be made to be small, the overall size of the aromatherapy diffuser will have a relatively larger size, and this makes the conventional aromatherapy diffuser inconvenient to carry. Thus, when a user of the conventional aromatherapy diffuser wishes to bring it with him while he is traveling, he will feel extremely inconvenient and may even give up bringing the aromatherapy diffuser with him.

Second, there may be water leak around the built-in water tank. This is a deep-seated problem associated with conventional aromatherapy diffuser. Many aromatherapy diffusers have been developed to tackle the water leak problem. However, none of them has achieved complete success as long as the built-in water tank exists.

As a result, there is a need to develop an aromatherapy diffuser which does not have a built-in water tank for pre-storing water. Moreover, there is a need to develop an aromatherapy diffuser which is capable of agitating water which is stored in a separately provided container for allowing a user to diffuse water and essential oil whenever necessary.

SUMMARY OF THE PRESENT INVENTION

Certain variations of the present invention provide an aromatherapy diffuser which does not have a built-in water tank for pre-storing water.

Certain variations of the present invention provide an aromatherapy diffuser which is capable of agitating water which is stored in a separately provided container for allowing a user to diffuse water and essential oil whenever necessary, such as when a user is traveling.

In one aspect of the present invention, it provides an aromatherapy diffuser for immersing into a predetermined amount of water stored in a container, comprising:

a diffuser body having an oil storage cavity for storing a predetermined amount of essential oil; and a diffusion device which is supported in the diffuser body, and comprises an ultrasonic vibrator arranged to generate ultrasonic vibrations, in such a manner that when the diffusion body is partially immersed in the water stored in the container, the essential oil is released to the water from the oil storage cavity while the ultrasonic vibrator is arranged to cause ultrasonic vibrations in the water so as to agitate the water molecules for releasing negatively charged mist and essential oil into ambient air.

This summary presented above is provided merely to introduce certain concepts and not to identify any key or essential features of the claimed subject matter.

DETAILED DESCRIPTION OF THE PREFERRED EMBODIMENT

Figure 1:
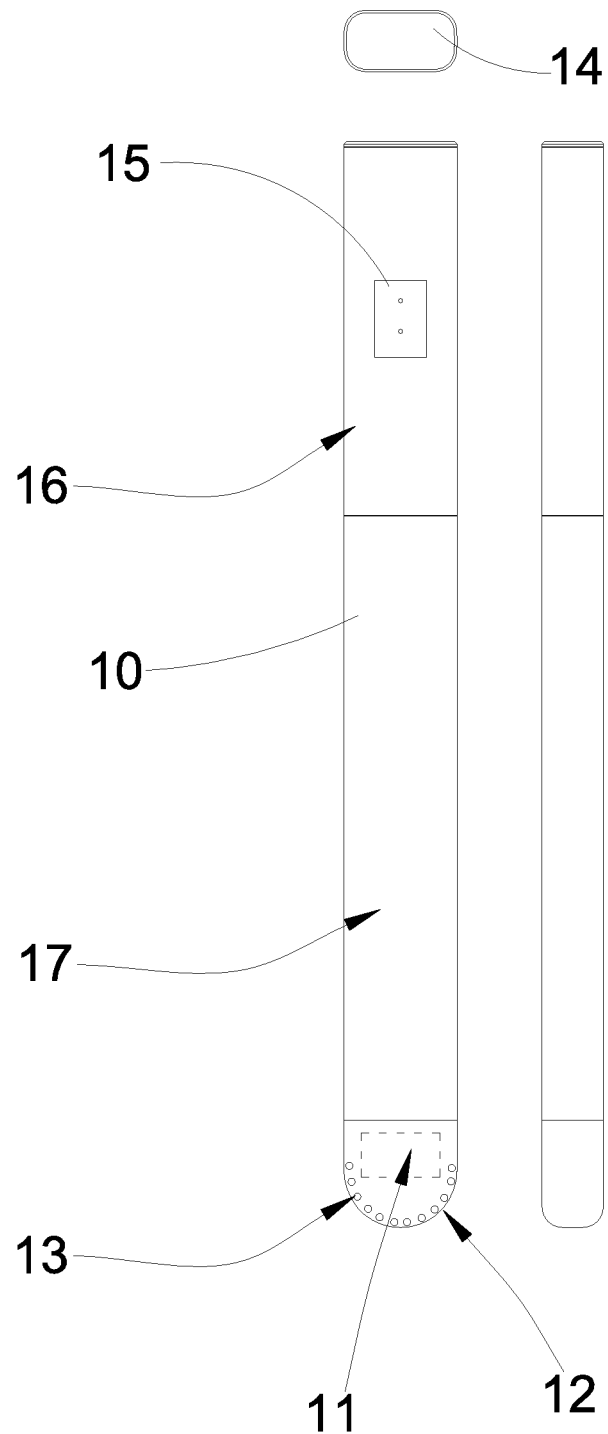
FIG. 1 is a front view of an aromatherapy diffuser according to a preferred embodiment of the present invention.
Figure 2:
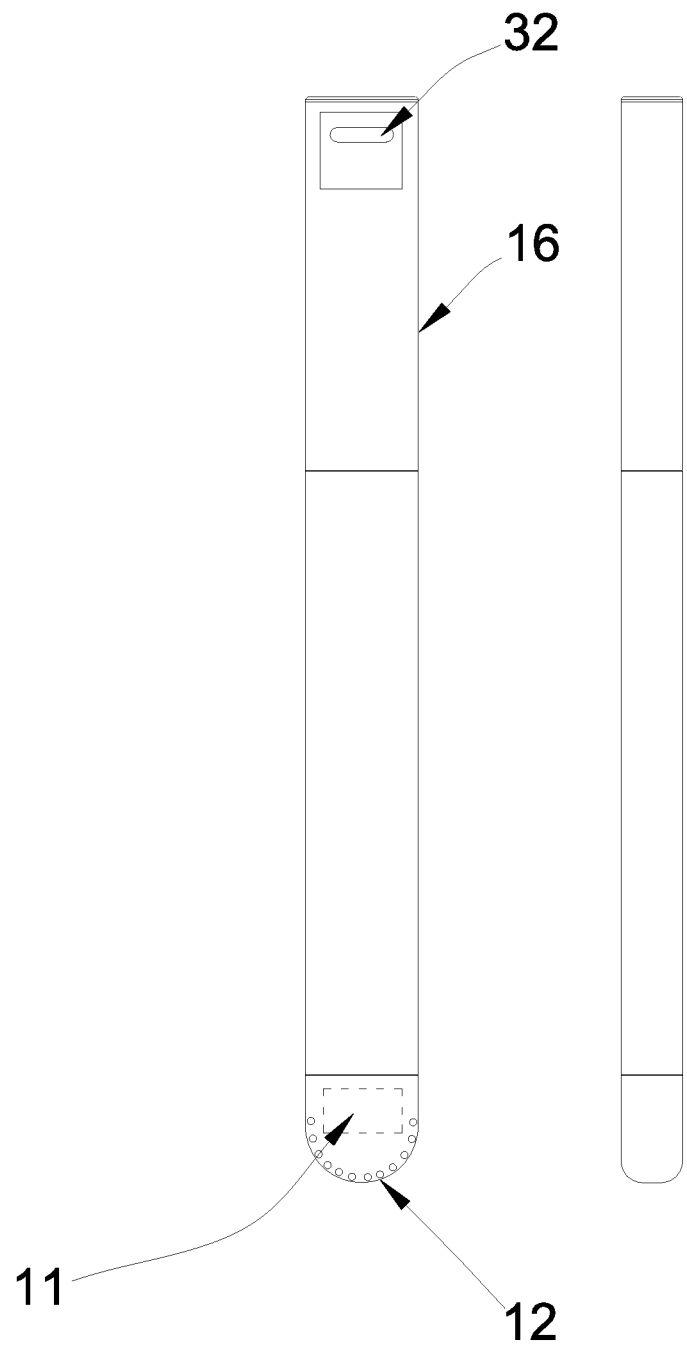
FIG. 2 is a rear view of the aromatherapy diffuser according to the preferred embodiment of the present invention.
Figure 3:
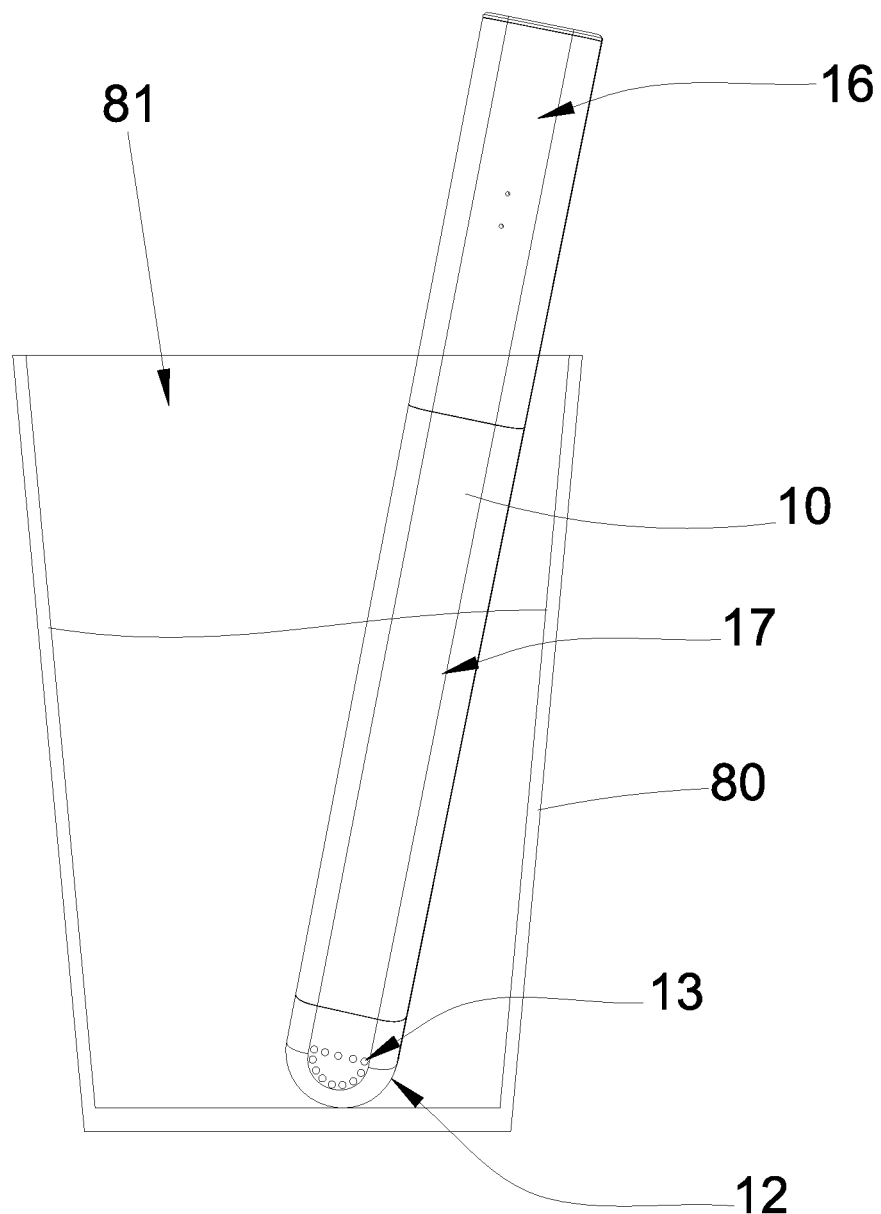
FIG. 3 is a schematic diagram of the aromatherapy diffuser according to the preferred embodiment of the present invention.

The following detailed description of the preferred embodiment is the preferred mode of carrying out the invention. The description is not to be taken in any limiting sense. It is presented for the purpose of illustrating the general principles of the present invention.

Referring to FIG. 1 to FIG. 5 of the drawings, an aromatherapy diffuser according to a preferred embodiment of the present invention is illustrated. Broadly, the aromatherapy diffuser may comprise a diffuser body 10 and a diffusion device 20. The aromatherapy diffuser may be immersed into a predetermined amount of water stored in a receiving cavity 81 of a container 80, such as a cup. The container 80 is not part of the present invention so that a user may utilize any container 80 in conjunction with the aromatherapy diffuser of the present invention to produce water vapor and mist of essential oil for aromatherapy purpose.

The diffuser body 10 may have an oil storage cavity 11 for storing a predetermined amount of essential oil.

The diffusion device 20 may be supported in the diffuser body 10, and comprises an ultrasonic vibrator 21 arranged to generate ultrasonic vibrations, in such a manner that when the diffusion body 10 is partially immersed in the water stored in the container 80, the essential oil may be released to the water from the oil storage cavity 11 while the ultrasonic vibrator 21 may be arranged to cause ultrasonic vibrations in the water and essential oil so as to agitate the water molecules for releasing negatively charged mist and essential oil into ambient air.

According to the preferred embodiment of the present invention, the diffuser body 10 may be elongated in shape so that it may be readily but partially immersed in the water stored in the container 80. The diffuser body 10 may be specifically configured to be easily portable so that a user may bring the aromatherapy diffuser of the present invention with him while he is traveling. All he needs to get from where he stays is the container 80 such as a cup filled with a suitable amount of water. Since there is no water tank formed in the diffuser body 10, the user does not need to worry about water leak.

The oil storage cavity 11 may be located at a lower tip portion 12 of the diffuser body 10 so that the oil storage cavity 11 may communicate with the container 80 for controllably releasing essential oil into the receiving cavity 81. Thus, the diffuser body 10 may have an oil outlet 13 formed on the lower tip portion 12 and communicate with the oil storage cavity 11. Essential oil may be controllably released from the oil storage cavity 11 to the receiving cavity 81 through the oil outlet 13.

The aromatherapy diffuser may further comprise a control circuit 60 supported in the diffuser body 10 for centrally controlling electronic components of the aromatherapy diffuser. The control circuit 60 may be implemented on a Printed Circuit Board (PCB 61) wherein other electronic components may be electrically connected to the control circuit 60 through the PCB 61.

A control panel 14 and a plurality of indicators 15 may also be mounted on the diffuser body 10 and electrically connected to the control circuit 60 for allowing a user to control an operation of the aromatherapy diffuser, such as turning it on or off.

The aromatherapy diffuser may further comprise a power source 30 supported in the diffuser body 10 at an upper portion 16 thereof for providing power to the diffusion device 20. The power source 30 may comprise a rechargeable battery 31 which may be recharged through a specifically designed adapter (described below). The power source 30 may be electrically connected to the control circuit 60 which may acquire power from the power source 30 and control the use of and distribute power acquired from the power source 30 for other electronic components.

Figure 4:
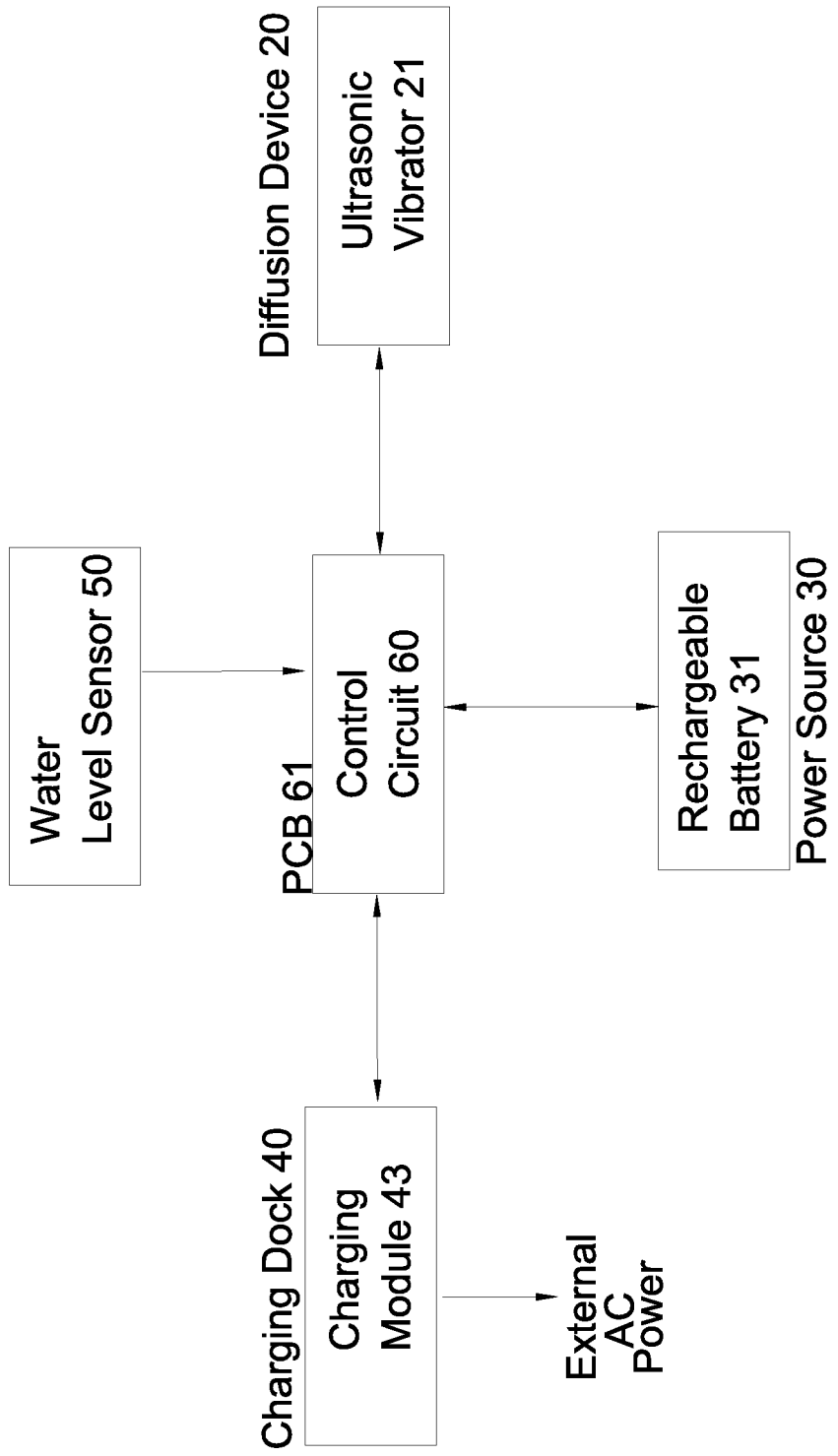
FIG. 4 is a block diagram of an aromatherapy diffuser according to the preferred embodiment of the present invention.
Figure 5:
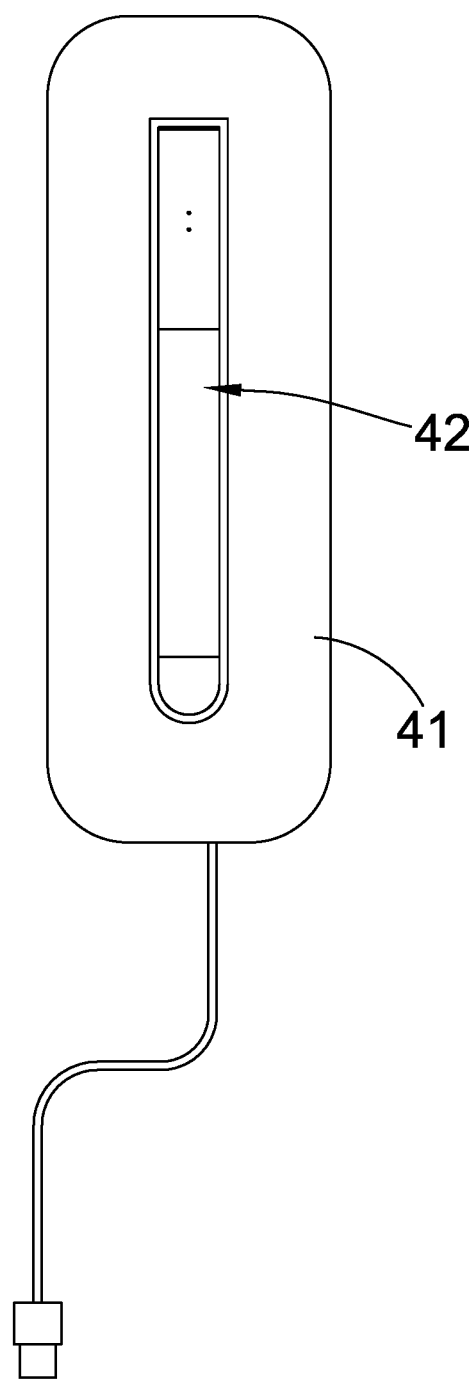
FIG. 5 a schematic diagram of a charging dock of the aromatherapy diffuser according to the preferred embodiment of the present invention.

Accordingly, as shown in FIG. 4 to FIG. 5 of the drawings, the aromatherapy diffuser may further comprise a charging dock 40 which may be configured to electrically connect to the diffuser body 10 for charging the power source 30 provided therein. More specifically, the charging dock 40 may comprise a base 41, a charging platform 42 formed on the base 41, and a charging module 43 received in the base 41 for electrically connected to an external power source, such as an external AC power source. When the diffuser body 10 is properly disposed on the charging platform 42, the charging module 43 may be arranged to charge the power source 30 supported in the diffuser body 10, through charging port 32 formed on the upper portion 16 of the diffuser body 10 or through wireless charging. The charging module 43 may be electrically connected to the control circuit 60 which may control the charging operation of the power source 30. When the power source 30 in the diffuser body 10 is fully charged, the diffuser body 10 may be detached from the charging dock 40 and may be kept portable by the user for a certain period of time without re-charging. In other words, a user may or may not need to bring the charging dock 40 with him while he is travelling.

The ultrasonic vibrator 21 of the diffusion device 20 may be positioned in a mid vibration portion 17 of the diffuser body 10 wherein the mid vibration portion 17 may be formed between the upper portion 16 and the lower tip portion 12. The ultrasonic vibrator 21 may be electrically connected to the control circuit 60 which may drive the ultrasonic vibrator 21 to cause the water and essential oil contained in the container 80 to undergo ultrasonic vibrations so as to cause negative ions of water and vapor which is mixed with essential oil molecules to be released from the container 80.

The aromatherapy diffuser may further comprise a water level sensor 50 supported on the diffuser body 10 and electrically connected to the control circuit 60 in such a manner that when the water level in the receiving cavity 81 of the container 80 is below a predetermined threshold, the control circuit 60 may automatically deactivate the operation of the ultrasonic vibrator 21.

The operation of the present invention is as follows: when the diffuser body 10 is immersed in the water contained in the container 80, essential oil may be released from the oil storage cavity 11 through the oil outlet 13. The ultrasonic vibrator 21 may then be activated through operation of the control panel 14 for causing the water and essential oil in the container 80 to be transformed into water and oil vapor with negative ions. The water and oil vapor with negative ions will then be diffused into ambient environment. When the user finishes using the aromatherapy diffuser, he or she may put the diffuser body 11 on the charging platform 42 of the charging dock 40 for recharging of the rechargeable battery as the power source 30.

The advantageous effects of the present invention may be elaborated as follows: the aromatherapy diffuser of the present invention does not possess any built-in water tank so as to completely eliminate the potential risk of water leak and the inconvenience of having a bulky size. A user may conveniently utilize a water cup as the container 80 and fill the water cup with a predetermined amount of water and partially immerse the diffuser body 10 in the water. Essential oil will then be released to the water and the ultrasonic vibrator 21 may then produce water and oil vapor with negative ions to ambient environment. As such, the present invention may be conveniently carried by the user while he or she is traveling.

The present invention, while illustrated and described in terms of a preferred embodiment and several alternatives, is not limited to the particular description contained in this specification. Additional alternative or equivalent components could also be used to practice the present invention.

What is claimed is:

1. An aromatherapy diffuser for immersing into a predetermined amount of water stored in a receiving cavity of a container, comprising:
   a diffuser body having an oil storage cavity for storing a predetermined amount of essential oil; and
   a diffusion device which is supported in said diffuser body, and comprises an ultrasonic vibrator arranged to generate ultrasonic vibrations, in such a manner that when said diffusion body is partially immersed in said water stored in said container, said essential oil is released to said water from said oil storage cavity while said ultrasonic vibrator is arranged to cause ultrasonic vibrations in said water so as to agitate said water molecules for releasing negatively charged mist and essential oil into ambient air.

2. The aromatherapy diffuser, as recited in claim 1, further comprising a printed circuit board and a control circuit supported in said diffuser body for centrally controlling electronic components of said aromatherapy diffuser, said control circuit being implemented on said printed circuit board.

3. The aromatherapy diffuser, as recited in claim 2, further comprising a power source supported in said diffuser body at an upper portion thereof for providing power to said diffusion device, said power source comprising a rechargeable battery.

4. The aromatherapy diffuser, as recited in claim 3, wherein said diffuser body further has a lower tip portion and an oil outlet, wherein said oil storage cavity and said oil outlet are located at said lower tip portion of said diffuser body so that said essential oil is adapted to be controllably released in said receiving cavity of said container through said oil outlet.

5. The aromatherapy diffuser, as recited in claim 4, wherein said ultrasonic vibrator of said diffusion device is positioned in a mid vibration portion of said diffuser body wherein said mid vibration portion is formed between said upper portion and said lower tip portion, said ultrasonic vibrator electrically connecting to said control circuit which selectively drives said ultrasonic vibrator to cause said water and essential oil contained in said container to undergo ultrasonic vibrations.

6. The aromatherapy diffuser, as recited in claim 3, further comprising a charging dock arranged to selectively and electrically connect to said diffuser body for charging said power source provided therein.

7. The aromatherapy diffuser, as recited in claim 5, further comprising a charging dock arranged to selectively and electrically connect to said diffuser body for charging said power source provided therein.

8. The aromatherapy diffuser, as recited in claim 6, wherein said charging dock comprises a base, a charging platform formed on said base, and a charging module received in said base for electrically connected to an external power source, wherein when said diffuser body is disposed on said charging platform, said charging module is arranged to charge said power source supported in said diffuser body.

9. The aromatherapy diffuser, as recited in claim 7, wherein said charging dock comprises a base, a charging platform formed on said base, and a charging module received in said base for electrically connected to an external power source, wherein when said diffuser body is disposed on said charging platform, said charging module is arranged to charge said power source supported in said diffuser body.

10. The aromatherapy diffuser, as recited in claim 4, further comprising a water level sensor supported on said lower tip portion of said diffuser body and electrically connected to said control circuit in such a manner that when said water level in said receiving cavity of said container is below a predetermined threshold, said control circuit automatically deactivates an operation of said ultrasonic vibrator.

11. The aromatherapy diffuser, as recited in claim 8, further comprising a water level sensor supported on said lower tip portion of said diffuser body and electrically connected to said control circuit in such a manner that when said water level in said receiving cavity of said container is below a predetermined threshold, said control circuit automatically deactivates an operation of said ultrasonic vibrator.

12. The aromatherapy diffuser, as recited in claim 9, further comprising a water level sensor supported on said lower tip portion of said diffuser body and electrically connected to said control circuit in such a manner that when said water level in said receiving cavity of said container is below a predetermined threshold, said control circuit automatically deactivates an operation of said ultrasonic vibrator.

\* \* \* \* \*